(12) United States Patent
Mistry et al.

(10) Patent No.: US 11,396,000 B2
(45) Date of Patent: Jul. 26, 2022

(54) FRIABLE SHELL MICROCAPSULES, PROCESS FOR PREPARING THE SAME AND METHOD OF USE THEREOF

(71) Applicant: ISP INVESTMENTS LLC, Wilmington, DE (US)

(72) Inventors: Kishor Kumar Mistry, West Yorkshire (GB); Assim Fiaz, West Yorkshire (GB); Abdul Wahab Hussain, West Yorkshire (GB); Terry Crutcher, Hillsborough, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 73 days.

(21) Appl. No.: 16/070,446

(22) PCT Filed: Jan. 13, 2017

(86) PCT No.: PCT/US2017/013465
§ 371 (c)(1),
(2) Date: Jul. 16, 2018

(87) PCT Pub. No.: WO2017/123965
PCT Pub. Date: Jul. 20, 2017

(65) Prior Publication Data
US 2019/0054440 A1  Feb. 21, 2019

Related U.S. Application Data

(60) Provisional application No. 62/351,269, filed on Jun. 16, 2016, provisional application No. 62/278,672, filed on Jan. 14, 2016.

(51) Int. Cl.

| | | |
|---|---|---|
| *B01J 13/14* | (2006.01) |
| *A61Q 5/12* | (2006.01) |
| *A61Q 15/00* | (2006.01) |
| *A61K 8/81* | (2006.01) |
| *B01J 13/18* | (2006.01) |
| *C11D 3/50* | (2006.01) |
| *C11D 11/00* | (2006.01) |
| *A23P 10/30* | (2016.01) |
| *A61Q 5/06* | (2006.01) |
| *C08L 33/00* | (2006.01) |
| *A61Q 17/04* | (2006.01) |
| *A61Q 19/10* | (2006.01) |
| *A01N 25/28* | (2006.01) |
| *B32B 27/14* | (2006.01) |
| *A23L 27/00* | (2016.01) |
| *A61K 8/11* | (2006.01) |
| *C11D 17/00* | (2006.01) |
| *C08F 2/28* | (2006.01) |
| *C08F 20/06* | (2006.01) |
| *C08F 20/08* | (2006.01) |
| *C08F 20/20* | (2006.01) |
| *C08F 20/26* | (2006.01) |
| *C08F 26/10* | (2006.01) |
| *C08F 222/10* | (2006.01) |
| *C08K 5/14* | (2006.01) |
| *C08K 5/23* | (2006.01) |

(52) U.S. Cl.
CPC .............. *B01J 13/14* (2013.01); *A01N 25/28* (2013.01); *A23L 27/72* (2016.08); *A23P 10/30* (2016.08); *A61K 8/11* (2013.01); *A61K 8/8147* (2013.01); *A61Q 5/06* (2013.01); *A61Q 5/12* (2013.01); *A61Q 15/00* (2013.01); *A61Q 17/04* (2013.01); *A61Q 19/10* (2013.01); *B01J 13/185* (2013.01); *B32B 27/14* (2013.01); *C08F 2/28* (2013.01); *C08F 20/06* (2013.01); *C08F 20/08* (2013.01); *C08F 20/20* (2013.01); *C08F 20/26* (2013.01); *C08F 26/10* (2013.01); *C08L 33/00* (2013.01); *C11D 3/502* (2013.01); *C11D 3/505* (2013.01); *C11D 11/0017* (2013.01); *C11D 11/0023* (2013.01); *C11D 17/0039* (2013.01); *A61K 2800/412* (2013.01); *C08F 222/104* (2020.02); *C08K 5/14* (2013.01); *C08K 5/235* (2013.01)

(58) Field of Classification Search
CPC .... B01J 13/14; A61K 8/11; C08F 2/28; C08F 20/06; C08F 20/08; C08F 20/26; C08F 20/10
See application file for complete search history.

(56) References Cited

U.S. PATENT DOCUMENTS

| | | |
|---|---|---|
| 6,849,591 B1 | 2/2005 | Boeckh et al. |
| 2013/0302392 A1 | 11/2013 | Mistry et al. |
| 2015/0203787 A1 | 7/2015 | Lei et al. |

OTHER PUBLICATIONS

International Search Report of PCT Application No. PCT/US2017/03465 published on Jul. 20, 2017.
Waterbeemd et al. Lipophillicity in PK design: Methyl, ethyl, futile. Journal of Computer-Aided Molecular Design.

*Primary Examiner* — Peter D. Mulcahy
(74) *Attorney, Agent, or Firm* — William J. Davis; Nathalie Tietcheu

(57) ABSTRACT

The present application describes a microcapsule comprising: (i) a lipophilic core material, and (ii) a microcapsule shell, wherein microcapsule shell formed from oil-in-water emulsion polymerisation of monomer mixture consisting essentially of: (a) greater than 70 to about 99% by weight of at least one polyfunctional ethylenically unsaturated monomer, (b) about 1 to about 30% by weight of at least one unsaturated carboxylic acid monomer or its ester, and (c) about 0 to about 30% by weight of at least one vinyl monomer. Also provides process for preparing the same and its method of use in various applications.

17 Claims, No Drawings

FRIABLE SHELL MICROCAPSULES, PROCESS FOR PREPARING THE SAME AND METHOD OF USE THEREOF

FIELD OF THE INVENTION

The present application relates to microcapsules, particularly, friable and highly crosslinked microcapsules having improved retention and release of lipophilic core material. The present application also relates to a process for making the microcapsules and their applications in various industries as described herein.

BACKGROUND OF THE INVENTION

General designing of a microcapsule is to provide: (a) protection and stability to entrapped actives in the microcapsule; (b) controlling release rate of the entrapped actives; (c) delivery-matrix for targeted delivery of actives; (d) a means of improved substantivity of the actives on a particular surface or substrate.

Conventional encapsulation methods available up to the present time can generally be classified as either physical-mechanical encapsulation methods or chemical encapsulation methods. Included among conventional chemical encapsulation methods are physicochemical methods such as coacervation, interfacial polymerization methods, in situ methods and the like.

In the case of physical-mechanical encapsulation methods, such as spray drying, particle size control is generally achieved through control of the physical conditions under which the involved processes are carried out. The microcapsule particles formed have an inner core material surrounded by an outer polymeric shell in which the core contains lipophilic/hydrophobic compounds. The release rate of the core material and the diffusion of the core material through the capsule wall can be controlled by varying the wall composition and/or the degree of crosslinking of the wall. Also, the degree of crosslinking of the wall directly impacts the strength and nature of the wall of the microcapsule. Furthermore, if a material is encapsulated, its useful life can be significantly extended. Also, if a material is toxic and hence difficult to handle, encapsulation of the material can reduce the threat of acute exposure and allow for easier handling.

U.S. Pat. No. 4,798,691 assigned to Japan Synthetic Rubber Company describes microcapsule formation by polymerizing blends of monomers having ethylenically unsaturated groups. The monomer blends comprise a crosslinkable monomer, a hydrophilic monomer and another monomer which is capable of co-polymerizing with the crosslinkable and hydrophilic monomer.

U.S. Pat. No. 5,292,835 assigned to BASF discloses composition, process and use of microcapsules made by in situ polymerization. Specifically disclosed are polymerizing monomer mixtures of (A) 30 to 100% by weight of one or more $C_1$—$C_{24}$-alkyl esters of acrylic or methacrylic acid (monomer I), and (B) 0 to 70% by weight of a bi- or polyfunctional monomer (monomer II). Specifically illustrated are polymerization reactions of acrylate monomers such as methyl methacrylate, methacrylic acid and butanediol diacrylate together with a free radical initiator.

U.S. Patent Application No. 2007224899 by Ciba discloses microcapsules comprising a core material within a substantially impervious polymeric shell, wherein the core material comprises a hydrophobic substance and the polymeric shell comprises: (A) 5 to 90% by weight of an ethylenically unsaturated water soluble monomer, (B) 5 to 90% by weight of a multifunctional monomer, and (C) 0 to 55% by weight other monomer, and wherein the amount of the polymeric shell and the proportions of A, B and C are such that the particles exhibit a half height at least 350° C. The ethylenically unsaturated water soluble monomer has water solubility of at least 5 gm/100 cc at 25° C. The microcapsules are incorporated into textile materials.

U.S. Patent Application No's: 2009274906, 20090274905, and 20090274905 by Appleton Papers describe a multi-step method of microencapsulation, microcapsules and particles produced by various processes. These patent applications disclose low permeability microcapsules prepared predominately from >95% multi-functional oligomers. The process involves a pre-polymer formation in an oil medium to form a first reaction product. This first reaction product is then used in the actual encapsulation process. According to the process, microcapsule shell formation involves an interaction of the first reaction product with an anionic emulsifier at the oil/water interface.

Other approaches in encapsulation technology target controlled or customized release of actives from substrates. These microcapsules are adapted to break under friction and provide an instant "burst" of the fragrance when the microcapsules are ruptured. There are numerous patents relating to delivering fragrance microcapsules from detergent products, such as fabric softeners, rinse off products and shampoos. In a majority of cases, these microcapsules are based on melamine formaldehyde chemistry.

U.S. Pat. No. 4,145,184 describes a detergent composition containing perfume in the form of water-insoluble, friable microcapsules which become entrained in or on fabric during a laundering process and which release the perfume during manipulation of the dry fabric. It further describes a laundry detergent composition comprising: (a) from 2% to 95% of a surfactant selected from the group consisting of anionic, nonionic, ampholytic, zwitterionic surfactants, and mixtures thereof; and (b) an effective amount of a perfuming agent comprising a perfume encapsulated in water insoluble, friable microcapsules having an average size of from about 5 to about 300 microns. The preferred materials for the microcapsule shell walls are aminoplast polymers comprising a reaction product of urea and formaldehyde.

U.S. Pat. No. 8,034,887 describes a process for preparing a microcapsule comprising lipophilic core and a capsule wall synthesized by free-radical polymerization from 30% to 100% by weight, based on the total weight of monomers, of one or more monomers selected from the group consisting of C1-C24 alkyl esters of acrylic acid, $C_1$—$C_{24}$ alkyl esters of methacrylic acid, acrylic acid, methacrylic acid, and maleic acid; 0% to 70% by weight, based on the total weight of the monomers, of one or more difunctional or polyfunctional monomers, which are sparingly soluble or insoluble in water; and 0% to 40% by weight, based on the total weight of the monomers, of one or more other monomers.

U.S. Patent Application No. 20150203787 describes a hydrogel capsule comprising a fragrance or odorant encapsulated in at least one polymerized acrylic or methacrylic acid, or ester thereof, wherein the hydrogel capsule has a mean diameter in the range of 1 to 100 μm and the fragrance or odorant is encapsulated in the hydrogel capsule during polymerization of the acrylic or methacrylic acid, or ester thereof.

U.S. Patent Application No. 20130302392 describes a hydrogel microcapsule, particularly, cationized hydrogel microcapsules having improved substantivity. More particularly, the patent application relates to substantive cationized hydrogel microcapsules comprising a lipophilic core material and a polymeric shell material, wherein the polymeric shell comprises: a) 5-99.9% by weight of oil soluble mono functional ethylenically unsaturated amine monomer, b) 0.1-95% by weight of polyfunctional ethylenically unsaturated monomer, and c) up to 30% by weight of other monomers.

In view of the foregoing, clearly there remains a need for friable microcapsules having improved retention and release of lipophilic and functional core material entrapped therein in various applications.

SUMMARY OF THE INVENTION

The primary objective of the present application is to prepare friable and highly crosslinked microcapsules having improved retention and release of lipophilic core material entrapped or encapsulated therein. More particularly, the present application relates to microcapsules comprising a lipophilic core material and a microcapsule shell, wherein the microcapsule shell is formed from oil-in-water emulsion polymerization of a monomer mixture consisting essentially of: (a) greater than 70 to about 99% by weight of at least one polyfunctional ethylenically unsaturated monomer, (b) about 1 to about 30% by weight of at least one unsaturated carboxylic acid monomer or its ester, and (c) about 0 to about 30% by weight of at least one vinyl monomer.

Another objective of the present application is to provide a process for preparing microcapsules comprising the steps of : (A) preparing an oil phase comprising: (i) a monomer mixture consisting essentially of: (a) greater than 70 to about 99% by weight of at least one polyfunctional ethylenically unsaturated monomer, (b) about 1 to about 30% by weight of at least one unsaturated carboxylic acid monomer or its ester , and (c) about 0 to about 30% by weight of at least one vinyl monomer; and (ii) at least one lipophilic core material; (B) preparing a separate aqueous phase comprising at least one polymeric emulsion stabilizer and water; (C) adding the oil phase of step (A) to the aqueous phase of step (B) under mechanical shear to form an oil-in-water emulsion; and (D) polymerizing the oil-in-water emulsion of step (C) through radical polymerization employing at least one initiator to produce core-shell microcapsules comprising an entrapped lipophilic core material and a polymeric shell, wherein the core-shell microcapsules are suspended in water.

Another objective of the present application provides use of the microcapsules described above for delivering encapsulated or entrapped functional actives in various applications and industries. Examples can include, without limitation: fragrances, agrochemicals, pharmaceuticals, cosmetics, personal care products, laundering detergents, homecare & cleaning products, dish washing detergents, oral care, dental care, textiles, paper, mining, oil industry, water treatment, adhesives, coatings, plastics, sealants, construction, paints, inks and dyes onto different substrate surfaces such as skin, hair, textiles. The microcapsules described herein can be advantageously used to impart a long lasting delivery of the actives on a substrate.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included examples.

The singular forms "a," "an," and "the" include plural forms unless the context clearly dictates otherwise specified or clearly implied to the contrary by the context in which the reference is made.

The terms "include," "includes," and "including," as used herein, are meant to be non-limiting and are understood to mean "comprise," "comprises," and "comprising," respectively.

All percentages, parts, proportions and ratios as used herein, are by weight of the total composition, unless otherwise specified. All such weights as they pertain to listed ingredients are based on the active level and, therefore, do not include solvents or by-products that can be included in commercially available materials, unless otherwise specified.

All references to singular characteristics or limitations of the present invention shall include the corresponding plural characteristic or limitation, and vice-versa, unless otherwise specified or clearly implied to the contrary by the context in which the reference is made.

The term "comprising" refers to optional compatible components that can be used provided that important ingredients are present in the suitable form and concentrations. The term "comprising" thus encompasses and includes more restrictive terms "consisting of" and "consisting essentially of" which can be used to characterize the essential ingredients such as lipophilic core material, shell material, polyfunctional ethylenically unsaturated monomer, unsaturated carboxylic acid, stabilizers and/or initiators.

The term "polyfunctional ethylenically unsaturated monomer" refers to a monomer containing two or more polymerizable ethylenically unsaturated groups. Wherein the high percentage of at least one polyfunctional ethylenically unsaturated monomer results in a highly cross-linked polymer structure of the microcapsule shell. Such high cross-linking renders the polymeric shell friable in nature.

The term "room temperature" refers to a temperature about 15° C. to about 30° C.

The terms "microencapsulation", "micro-encapsulation", "microcapsulation", "encapsulation", and "capsulation" are synonymously used in this patent application. These terms are same and used interchangeably.

The terms "microencapsule", "micro-encapsule", "microcapsule", "encapsule", and "capsule" are synonymously used in this patent application. These terms are same and used interchangeably.

References herein to "one embodiment" or "one aspect" or "one version" or "one objective" of the application include one or more such embodiment, aspect, version or objective, unless the context clearly dictates otherwise.

What is described herein are friable and highly cross-linked microcapsules having improved retention and release of lipophilic core material. The microcapsule of the present application is composed of a lipophilic core material and a microcapsule shell, wherein microcapsule shell is formed from oil-in-water emulsion polymerization of a monomer mixture consisting essentially of: (a) greater than 70 to about 99% by weight of at least one polyfunctional ethylenically unsaturated monomer, (b) about 1 to about 30% by weight of at least one unsaturated carboxylic acid monomer or its ester, and (c) about 0 to about 30% by weight of at least one vinyl monomer.

In accordance with certain aspects, the microcapsule shell composition includes at least one polyfunctional ethylenically unsaturated monomer (a) in an amount from greater than 80 to 99% by weight of the polymer shell.

The polyfunctional ethylenically unsaturated monomer (a) is selected from the group consisting of ethylene glycol di(meth)acrylate, di(ethylene glycol) di(meth)acrylate, triethylene glycol di(meth)acrylate, propylene glycol di(meth)acrylate, 1,4-butanediol di(meth)acrylate, 1,6-hexanediol di(meth)acrylate, glycerol di(meth)acrylate, 1,3-butanediol di(meth)acrylate, neopentyl glycol di(meth)acrylate, 1,10-decanediol di(meth)acrylate, pentaerythritol tri(meth)acrylate, pentaerythritol tetra(meth)acrylate, dipentaerythritol hexa(meth)acrylate, triallylformal tri(meth)acrylate, allyl methacrylate, trimethylol propane tri(meth)acrylate, tributanediol di(meth)acrylate, PEG 200 di(meth)acrylate, PEG 400 di(meth)acrylate, PEG 600 di(meth)acrylate, 3-acryloyloxyglycol monoacrylate, triacryl formal, triallyl isocyanurate and combinations thereof.

In accordance with certain aspects, the microcapsule shell composition comprises the unsaturated carboxylic acid monomer or its ester (b) in an amount from about 10 to 30% by weight of the polymer shell. Other non-limiting ranges of unsaturated carboxylic acid monomer or its ester can include about 15 to 20 wt. %, or about 20 to 25 wt. %, or about 25 to 30 wt. % by weight of the polymer shell.

The unsaturated carboxylic acid monomers or its esters (b) include, but are not limited to acrylic acid, methacrylic acid, maleic acid, maleic anhydride, fumaric acid, itaconic acid, 2-carboxylethyl acrylate, C1-C24 alkyl ester of acrylic acid, C1-C24 alkyl ester of methacrylic acid, and combinations thereof.

According one embodiment of the present application, the non-limiting ranges of vinyl monomer (c) can include about 1 to 5, wt. %, or about 5 to 10 wt. %, or about 10 to 15 wt. %, or about 15 to 20 wt. %, or about 20 to 25 wt. %, or about 25 to 30 wt. % by weight of the polymer shell.

According to one embodiment of the present application, the microcapsule shell composition comprises vinyl monomers (c) selected from a group including but not limited to, N-vinyl pyrrolidone, N-vinyl caprolactam, 2-hydroxylethyl pyrrrolidone methacrylate, octyl acrylamide, acryloxyethyl-trimethyl ammonium chloride, 2-hydroxyethyl methacrylate, alkyl methacrylate and combination thereof. Non-limiting ranges of vinyl monomer can include about 1 to 5, wt. %, or about 5 to 10 wt. %, or about 10 to 15 wt. %, or about 15 to 20 wt. %, or about 20 to 25 wt. %, or about 25 to 30 wt. % by weight of the polymer shell.

The microcapsules of the present application include the polymeric shell material at an amount of 1-50%; or from 5-20% by weight of the microcapsules. The amount of core material in the microcapsule is 50-99%; or from 80-95% by weight of the microcapsules.

According to another embodiment of the present application, the microcapsule contains one or more lipophilic core material. Examples of the lipophilic core material can include, but are not limited to, fragrances, UV absorbers, emollient oils, insecticides, dyes, detergents, printing inks, perfumes, silicone conditioners, hair treatment/shampoo materials, biocides, adhesives, corrosion inhibitors, antifouling agents, flavors, cosmetic & personal care actives, oxidizing agents, pharmaceutical agents, agrochemicals/pesticides, lipids/fats, food additive, liquid crystals, coating materials, catalysts, preservatives and/or antimicrobial agents, lipophilic scale inhibitors, chemical reactants, rust-proofing agents, recording materials, and magnetic substances or combinations thereof, which can be used directly or dissolved or dispersed in an oily substance.

The fragrances suitable for use include without limitation, any combination of perfumes, flavors, essential oils, sensates and plant extract or mixture thereof capable of being encapsulated in accordance with the present application. A list of suitable fragrances can be found in U.S. Pat. Nos. 4,534,891; 5,112,688; 5,145,842; 6,194,375; 20110020416 and PCT Application No's. WO2009153695 and WO2010/044834, and Perfumes Cosmetics and Soaps, Second Edition, edited by W. A. Poucher, 1959. Each of the foregoing documents is incorporated herein by reference in its entirety.

The UV absorbers are chemical and physical sunscreens/UV filters, e.g., 3-benzylidene camphor, 4-methylbenzylidene camphor, 4-aminobenzoic acid (PABA), avobenzone, benzophenone 4 (sulisobenzone), benzophenone 5, benzophenone 8, benzophenone-3, benzylidene camphor sulfonic acid, bis-ethylhexyloxyphenol methoxyphenol triazine (Escalol S), butyl methoxy dibenzoylmethane, camphor benzalkonium methosulfate, cinoxate, diethylamino hydroxybenzoyl hexyl benzoate, dioxybenzone, disodium phenyl dibenzimidazole tetrasulfonate, drometrizole trisiloxane, ensulizole, ethylhexyl dimethyl PABA, ethylhexyl methoxycinnamate, ethylhexyl salicylate, ethylhexyl triazone, homosalate, isoamyl p-methoxycinnamate, meradimate, menthyl anthranilate, methylene bis-benzotriazolyltetramethylbutylphenol/bisoctrizole (Tinosorb M), octocrylene, octinoxate, PEG-25 PABA, octisalate, oxybenzone, padimate O, phenylbenzimidazole sulfonic acid, polyacrylamidomethyl benzylidene camphor, polysilicone-15, TEA-salicylate, terephthalylidene dicamphor sulfonic acid, titanium dioxide, trolamine salicylate, zinc oxide or combinations thereof.

Suitable emollients used in the present application can include, but are not limited to, oils such as orange, lavender, peppermint, lemon, pine, rosemary, rose, jasmine, tea tree, lemon grass, bergamot, basil, spearmint, juniper, clove, aniseed, fennel, cypress, fir, black pepper, sandalwood, cedarwood, rosewood, cardamom, cinnamon, coriander, eucalyptus, geranium, ginger, chamomile, grapefruit, neroli, petitgrain, thyme, vetiver and ylang ylang. The non-limiting list of lipophilic core material includes: linear or branched hydrocarbons of different chain lengths and viscosities such as mineral oil, petrolatum, white oil (also known as paraffin oil), dodecane, isododecane, squalane, hydrogenated polyisobutylene, polybutene, polydecene, docosane, hexadecane, isohexadecane and other isoparaffins. Alcohol, diol, triol or polyol esters of carboxylic or dicarboxylic acids, of either natural or synthetic origin having straight chain, branched chain and aryl carboxylic acids include diisopropyl sebacate, diisopropyl adipate, isopropyl myristate, isopropyl palmitate, myristyl propionate, cetyl lactate, myristyl lacate, lauryl lactate, $C_{12}$—$C_{15}$ alkyl lactate, dioctyl malate, decyl oleate, isodecyl oleate, ethylene glycol distearate, ethylhexyl palmitate (octyl palmitate), isodecyl neopentanoate, tridecyl neopentanoate, castoryl maleate, isostearyl neopentanoate, di-2-ethylhexyl maleate, cetyl palmitate, myristyl myristate, stearyl stearate, cetyl stearate, isocetyl stearate, dioctyl maleate, octyl dodecyl stearate, isocetyl stearoyl stearate, octyldodecyl stearoyl stearate dioctyl sebacate, diisopropyl adipate, cetyl octanoate, glyceryl dilaurate, diisopropyl dilinoleate and caprylic/capric triglyceride. Naturally occurring oils including triglycerides, diglycerides, monoglycerides, long chain wax esters and blends of these. Examples for naturally derived ester-based oils and waxes include, but are not limited to, argan oil, corn oil, castor oil, coconut oil, cottonseed oil, menhaden oil, avocado oil, beeswax, carnauba wax, cocoa butter, palm kernel oil, palm oil, peanut oil, shea butter, jojoba oil, soybean oil, rapeseed oil, linseed oil, rice bran oil, pine oil, sesame oil, sunflower seed oil and safflower oil. Also useful are hydrogenated, ethoxylated, propoxylated and maleated derivatives of these materials, e.g. hydrogenated safflower oil, hydrogenated castor oil; Cholesterol and its esters and derivatives, as well as natural materials comprising cholesterol derivatives such as lanolin and lanolin oil; Phospholipids (e.g. lecithin), sphingophospholipids, ceramides and related materials; C4-C20 alkyl ethers of polypropylene glycols, $C_1$—$C_{20}$ carboxylic acid esters of polypropylene glycols, and di-$C_8$—$C_{30}$ alkyl ethers; PPG-14 butyl ether, PPG-15 stearyl ether, diodyl ether, dodecyl octyl ether, and mixtures thereof, saturated and unsaturated fatty acids including but not limited to oleic, palmitic, isostearic, stearic, ricinoleic, linoleic and linolenic acid; Carboxylic monoesters and polyesters of sugars (mono-, di- and polysaccharides) and related materials.

The insecticides suitable for use in this application include without limitation, ethyl p-nitrophenyl, methidathion, chlorpyrifos, phosalone, dimethoate, methamidophos, fenpropathrin, salithion, fenoxycarb, azinphos-ethyl, azinphos-methyl, m-Tolyl methylcarbamate, methomyl, xylylcarb, cloethocarb, trichlorfon, acephate, amitraz, 2-(1-methylethyl)phenyl methylcarbamate, propoxur, aminocarb, aldicarb, fipronil, imidacloprid, acetamiprid, thiamethoxam, clothianidin, dinotefuran, nitenpyram, trimethacarb, and dioxacarb.

The dyes suitable for use in this application can include without limitation, oil -soluble dyes including Green 6 (CI 61570), Red 17 (CI 26100), Violet 2 (CI 60725) and Yellow 11 (CI 47000). Examples of oil-dispersible pigments include, but are not limited to, beta carotene (CI 40800), chromium hydroxide green (CI 77289), chromium oxide green (CI 77288), ferric ferrocyanide (CI 77510), iron oxides (CI 77491, 77492 77499), Pigment Blue 15 (CI74160), Pigment Green 7 (CI 74260), Pigment Red 5 (CI 12490), Red 30 (CI 73360), titanium dioxide (CI 77891) and ultramarines (CI 77007). Oil soluble pharmaceutical actives such as insect repellants for example, N,N-diethyl-meta-toluamide, IR3535, icaridin, picaridin, saltidin, citronella, permethrin, neem oil and lemon eucalyptus) and drug substances for the dermatological treatment of conditions of skin, hair and nails, which can include, but are not limited to, topical anaesthetics, anti-fungal, anti-bacterial, anti-viral, anti-dandruff, anti-acne and anti-inflammatory agents (steroidal and non-steroidal).

The detergent compositions can be liquid detergent compositions, such as laundry or (automatic) dish wash detergents. Specific examples of detergent compositions are disclosed in WO 2015/166076 A1, which is hereby incorporated by reference in its entirety.

The printing ink materials contemplated herein, can be used in inkjet, flexographic printing, spraying, inkjet printing, forward or reverse roll coating, direct forward gravure coating, screen printing, hand block printing, perrotine printing, engraved copper plate printing, roller printing, cylinder printing, machine printing, stencil printing or digital textile printing and etc. Examples of printing ink materials can be found in U.S. Pat. Nos. 8,808,815; 7,741,384, and WO 2014/160604 A1 which are incorporated herein by reference in their entirety.

The perfume and sensate components include, but are not limited to, linalool, coumarin, geraniol, citral, limonene, citronellol, eugenol, cinnamal, cinnamyl alcohol, benzyl salicylate, menthol, menthyl lactate, eucalyptol, thymol, methyl salicylate, methylfuran, menthone, and cinnamaldehyde.

The silicone conditioners suitable for use in this application include without limitation, polyalkylsiloxanes, polydialkylsiloxanes, polydiarylsiloxanes, and polyalkarylsiloxanes. The polydialkylsiloxanes can be polydimethylsiloxanes, which are commonly known as dimethicones. Further examples can include, but are not limited to cyclic siloxanes (e.g., cyclopentasiloxane), dimethiconoles, alkyl methicones, alkyl dimethicones, dimethicone copolyols, amino-functional silicones (e.g., amodimethicone, trimethylsilyloxyamodimethicone) and amphoteric silicones (e.g., cetyl PEG/PPG-15/15 butyl ether dimethicone, and his-PEG-18 methyl ether dimethyl silane).

Oily and oil-soluble extracts of plant materials such as flowers and herbs can include a wide range of materials. Non-limiting examples of extracts include but are not limited to rosemary, green, white or black tea, orchid, grape seed, sage, soybean, echinacea, arnica, rosehip, olive, and artichoke. Further, the plant-extracted oil-soluble components such as lycopene and other mixed carotenoids, capsaicin capsaicinoids, polyphenols (e.g., rosmarinic acid), terpenes, terpenoids, and oleoresins can be used as lipophilic core material.

In addition to those described previously, other hair treatment/shampoo ingredients can include cationic conditioning agents comprising tertiary and quaternary amino groups (e.g., quaternium-70, quaternium-80, stearamidopropyl dimethylamine, behentrimonium methosulfate, dicocodimonium chloride, dicetyldimonium chloride, distearyldimonium chloride hydroxyethyl cetyldimonium phosphate). Further, UV and color protectants (e.g., dimethylpabamidopropyl laurdimonium tosylate), heat protectants and styling polymers (e.g., vinyl pyrrolidone and vinylcaprolactam derivatives, such as PVP vinyl Caprolactam/DMAPA Acrylates Copolymer) can also be included.

The suitable biocides employed as a lipophilic material can include, but are not limited to an isothiazolone, a benzothiazole, a pyrethroid, a neonicotenoid, a halogenated carbamate, an azole, a chloronitrile, hypochlorite bleach, peracetic acid, bromochlorodimethylhydantoin, dichloroethylmethylhydantoin, chloroisocyanurate, trichloroisocyanuric and dichloroisocyanuric acids and salts thereof, calcium hypochlorite, lithium hypochlorite, chlorinated hydantoins, sodium hypobromite, brominated hydantoins, chlorine dioxide, peroxides, and persulfates.

The adhesive based compositions can also be employed as lipophilic material in microcapsules of the present application. The compositions can include, but are not limited to, block copolymers, amorphous polyolefins, metallocene polyolefins, ethylene vinyl-acetate, ethylene-methyl acetate, ethylene n-butyl acetate, polyethylene terephthalate, polyvinylpyrrolidone, polyvinylpyrrolidone/vinyl acetate, polyetheroxazoline, water dispersible copolyester, water soluble polyamides, polyvinylalcohol, polyethylene oxide. The compositions can also include, liquid tackifying resins, liquid polymers, liquid plasticizers and mixtures thereof. The liquid ingredients can be present in an encapsulated form along with other adhesive compositions.

The lipophilic corrosion inhibitors are selected from the group consisting of carboxylic acids and derivatives such as aliphatic fatty acid derivatives, imidazolines and derivatives. Also, inhibitors such as amides, quaternary ammonium salts, rosin derivatives, amines, pyridine compounds, trithione compounds, heterocyclic sulfur compounds, quinoline compounds, or salts, quats, or polymers of any of these, and mixtures thereof. For example, suitable inhibitors include primary, secondary, and tertiary monoamines, diamines, amides, polyethoxylated amines, salts of such materials, and amphoteric compounds. Still other examples include imidazolines having both straight and branched alkyl chains, phosphate esters, and sulfur containing compounds.

The anti-fouling agents can be tributyltin chloride or tributyltin fluoride.

Suitable flavors encapsulated as lipophilic material can be essential oils, derived from natural resources such as plants and fruits, examples of natural resources can include but not limited to citrus oils, fruit essences, peppermint oil, spearmint oil, other mint oils, clove oil, oil of wintergreen, and anise. Artificial or synthetic flavoring agents and components can also be used. Natural and artificial flavoring agents can be combined in any sensorially acceptable fashion.

The cosmetic & personal care actives, which are used for the conditioning or cosmetic treatment of skin, hair or nails can be found in IP.com publications IPCOM000128968D published on 23 Sep. 2005 and IPCOM000133874D published on 13 Feb. 2006, the contents of which are hereby incorporated by reference.

The oxidizing agents include inorganic or organic peroxides such as calcium peroxide, magnesium peroxides and lauryl peroxides.

The lipophilic pharmaceutical agents used for encapsulation can include, but are not limited to, antitussives, antihistamines, non-sedating antihistamines, decongestants, expectorants, mucolytics, analgesics, antipyretics, anti-inflammatory agents, local anesthetics, and mixtures thereof.

The term agrochemicals/pesticides refer to at least one active substance selected from the group consisting of pesticides, nematicides, safeners and/or growth regulators. The pesticides can be fungicides, insecticides, herbicides and growth regulators. In one non-limiting embodiment, the pesticides can be insecticides. Mixtures of the different classes of pesticides can also be used. The pesticides can be found, for example, in the Pesticide Manual, 15th Ed. (2009), The British Crop Protection Council, London. Suitable insecticides are those from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, (mitochondrial electron transport inhibitor)-acaricides, chloropicrin, pymetrozin, flonicamid, clofentezin, hexythiazox, etoxazole, diafenthiuron, propargite, tetradifon, chlorofenapyr, dinitro-ortho-cresol, buprofezine, cyromazine, amitraz, hydramethylnon, acequinocyl, fluacrypyrim, rotenone, or their derivatives. Suitable fungicides are those from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, and ureas.

The lipids/fats used for encapsulation include but are not limited to lipid-protein, lipid-carbohydrate or lipid-protein-carbohydrate.

The food additive used for encapsulation can include, but are not limited to, water and oil-soluble vitamins, amino acids, hormones, enzymes, medicinal agents such as antibiotics, antifungals, anti-parasitic agents, anti-coccidiosis agents, antivirals, anti-oxidants, prophylactic medicinals, and the like; and essential minerals and micronutrients. Examples of vitamin and its derivatives include vitamin E and some of the B vitamins, especially thiamin, tocopherol, tocopheryl acetate, retinol, retinyl palmitate, ascorbyl palmitate, niacinamide, and beta carotene. The anti-oxidants that are including but not limited to phenolics and non-phenloics. Examples of suitable antioxidants which can be used in the present application include vitamin C and vitamin E. Examples of phenolic anti-oxidants disclosed in U.S. Pat. No. 8,580,876 can be used in this application as suitable lipophilic agents.

The liquid crystal material which can be encapsulated can include but not limited to nematic, cholesteric, smectic A, and ferroelectric (chiral smectic C*).

Lipophilic scale inhibitors include those based on phosphate esters, and polyacrylates.

According to one embodiment of the present application, the coating materials for encapsulation are selected from the following non-limiting examples, i.e. cationic polymers such as polyvinyl pyrrolidone (PVP) copolymers (Gafquat HS-100, Styleze CC-10, Styleze W -20, Aqua Style 300 all available from Ashland), cationic cellulose polymers, cationic guars, cationic acrylate copolymers, chitosan, DADMAC (diallyldimethyl ammonium chloride) copolymers and polyethylene imines. Further, suitable polymers for coating purpose can include oil-soluble polymeric materials which have film-forming properties on skin and hair, such as VP/hexadecene copolymer, tricontanyl PVP and VP/eicosene copolymer.

The catalyst systems useful for the encapsulation of lipophilic material can include, but are not limited to heterogeneous, homogeneous, metal and nonmetal catalyst. Those catalysts are described in the publications such as WO 2003/006151, WO 2005/016510, WO 2007/096592, GB 2052296, U.S. Pat. No. 4,895,994 WO 2005/016510 and U.S. Pat. No. 3,594,666.

The preservatives and/or antimicrobial agents for encapsulation are selected from the following non-limiting examples such as benzoic acid, sorbic acid, dehydroacetic acid, piroctone olamine, DMDM hydnatoin, Iodopropynyl Butyl Carbamate (IPBC), triclosan, bronopol, isothiazolinones, parabens, phenoxyethanol, and combination thereof.

According to one embodiment, there is provided a consumer care composition that comprises a microcapsule having: (i) a lipophilic core material, and (ii) a microcapsule shell, wherein microcapsule shell formed from oil-in-water emulsion polymerization of monomer mixture consisting essentially of: (a) greater than 70 to about 99% by weight of polyfunctional ethylenically unsaturated monomer, (b) about 1 to about 30% by weight of unsaturated carboxylic acid monomer or its ester, and (c) about 0 to about 30% by weight of at least one vinyl monomer.

Examples of the lipophilic core material that are useful in a consumer care composition include fragrances, UV absorbers, emollient oils, insecticides, detergents, perfumes, silicone conditioners, hair treatment/shampoo materials, biocides, cosmetic & personal care actives, oxidizing agents, pharmaceutical agents, lipids/fats, preservatives and/or antimicrobial agents, or combination thereof, which can be used directly or dissolved or dispersed in the oily substance as used herein depending on the purpose of use.

According to another embodiment of the present application, the consumer care composition is a laundry care, personal care, all-purpose cleaner, therapeutic, cosmetic, homecare & cleaning, pharmaceutical or cosmeceutical composition.

According to yet another embodiment of the present application, the home care compositions are household cleaners, hard surface cleaners, carpet cleaners, polishes, or sprayable compositions.

According to yet another embodiment of the present application, the laundry care composition is a rinse conditioner, liquid detergent, solid detergent or fabric refresher.

According to yet another embodiment of the present application, the personal care composition is a hair shampoo, hair conditioner, rinse off or leave on composition for skin and hair, hair rinse, hair styling gel, hair colorant, hair removal depilatory, antiperspirant/deodorant, hand sanitizer, hand cream, hand lotion, liquid/solid soap, shower gel, body lotion, bar soap, body wash, sun protection product, preservative composition, sun and tissue regeneration scaffold, oral care, toothpaste, mouth wash and chewing gum, denture adhesive or dental care. Also, the personal care composition can be formed as a stick, roll-on or aerosol sprays.

In yet another non-limiting embodiment, it is described that the microcapsules of the present application can be incorporated in pharmaceutical compositions including but not limited to peroral and topical dosage forms, such as tablets, pellets, capsules, dermatological products (creams, gels, ointments, sprays, lotions, and foams), transdermal patches and the like.

In one non-limiting embodiment, the microcapsules of the present application can be advantageously used for controlling perfume release in fragrance delivery based consumer products. There is a considerable improvement in longevity and intensity of the encapsulated perfume observed in actual use. Examples of consumer products comprising perfume microcapsules according to certain aspects of the present application can fall into product group categories of laundering detergents, cosmetics, personal care products, dish washing detergents and house cleaners. More specific examples of consumer products include fabric conditioners, liquid/powdered laundering detergents, dish washing detergents, hair shampoos, hair conditioners, hair styling gels, soaps, body washes, shower gels, all-purpose cleaners including hard surface cleaners, carpet cleaners, body lotions, antiperspirant/deodorants and spray-able products.

Alternatively, the fragrance encapsulated microcapsules of the present application can be incorporated in 2-in-1 powdered detergent and conditioner compositions according to the processes described in U.S. Pat. Nos. 4,698,167 and 5,540,850 and also crystalline laundry additives as described in the US application 2011/97369 and PCT WO 2010/000558, which are incorporated herein by reference.

Alternatively, the fragrance microcapsules of the present application can be formulated into solid fabric care compositions with polysaccharides such as sugars according to the procedure described in US Patent No 20011/0082066, the contents of which are hereby incorporated by reference. The solid fabric care products can be used for delivering fragrances onto the textile articles during the washing/cleaning cycle and subsequently the laundered textiles have beneficial fragrance odor profile during the wear.

In another non-limiting embodiment, the application relates to a method for producing friable and highly cross-linked microcapsules with improved retention and release of fragrance material for incorporating into, (i) laundry detergents; (ii) fabric softener compositions; and (iii) drier-added fabric softener articles. When the microcapsules are deposited on fabrics during laundry treatment, they are capable of remaining on the textile following initial application and of later being sheared by the application of mechanical force. Accordingly, the encapsulated fragrance can provide a "burst" of fragrance during wear due to breakage of the capsule wall.

The delivery system of the present application is prepared by a process comprising mixing directly the microcapsules into surfactant containing products such as body rinse off products, shampoos, fabric conditioners, laundering detergents at required dose concentrations. If the surfactant containing products are liquid surfactant products, the microcapsules remain uniformly suspended in the liquid surfactant products by addition of suitable rheology modifiers. In the case of powdered surfactant products, the aqueous microcapsule dispersion can be spray dried and granulated before mixing into the powdered surfactant products.

According to another embodiment of the present application, the microcapsules can be supplied as a dried powder form or in aqueous solution as a dispersion of hydrogel microcapsules. The powdered form can be obtained by spray drying or filtration of the aqueous form of the microcapsules. It is contemplated that all of these material can be used with optional post coating material which can further comprise a post addition of a polymeric coating to improve its deposition. This optional coating also constitutes a means to improve and control the deposition of microcapsules onto a substrate, which is useful for an application in some functional products such as shampoos, fabric softeners and laundering detergents.

According to yet another embodiment of the present application, a method of use of a microcapsule comprises employing the microcapsule as a delivery matrix to deliver lipophilic core materials of the present application for industrial compositions selected from the group consisting of agrochemicals, textiles, paper, mining, oil industry, water treatment, adhesives, coatings, plastics, sealants, construction, paints, inks and dyes onto different substrate surfaces such as skin, hair, or textiles, and wherein the microcapsule comprises (i) a lipophilic core material, and (ii) a microcapsule shell, wherein microcapsule shell formed from oil-in-water emulsion polymerization of monomer mixture consisting essentially of: (a) greater than 70 to about 99% by weight of polyfunctional ethylenically unsaturated monomer, (b) about 1 to about 30% by weight of unsaturated carboxylic acid monomer or its ester, and (c) about 0 to about 30% by weight of at least one other monomers.

In one non-limiting embodiment of the present application, the microcapsules can be used to encapsulate the agrochemicals that are listed in U.S. Pat. No. 5,389,688 assigned to ISP Investments Inc., which is incorporated herein by reference in its entirety.

The microencapsules can also be used in the oil industry. The microcapsules contain a lipophilic oilfield chemical core such as corrosion inhibitors, scale inhibitors, oxidizing agents, crosslinking agents, catalysts, acidizing agents, biocides, demulsifiers, enzymes, polymers, lubricants, shale inhibitors, solvents, and surfactants to form encapsulated oil field chemicals. The encapsulated oil field chemicals can be applied advantageously at different petroleum extraction stages of drilling, cementing, stimulation to production and enhanced oil recovery. The release of the oilfield chemicals can be carried out by changing temperature, concentration, pH and shear upon application.

In one non-limiting embodiment, the microcapsules can be used to incorporate actives such as textiles both coatings and in-fiber. In some instances, the microcapsules can be added to the last step before coating, spraying or incorporation onto suitable materials such as textile fibers, coated textiles and construction products.

In one non-limiting embodiment, the microcapsules can be used to incorporate actives of adhesives including, but not limited to, polyurethanes, epoxy, polyesters, isocyanates, isocyanurates, polyethylene glycols and polypropylene glycols.

It is further contemplated that the microcapsules of the present application can be used in the construction industry in conjunction with cements, plaster boards, breeze blocks, chipboards, heat transfer fluids, sealants, and adhesives etc. The lipophilic core material can be a biocide, flame retardant, catalyst, and epoxy resins etc.

The microcapsules described herein can be used in conjunction with additives used in plastics such as flame retardants, catalysts, pigments, light stabilizers, UV absorbers which can be encapsulated to allow higher compatibilities, longevity and self-healing of the plastics. Particularly, the lipophilic core material can be a catalyst for self-healing, UV absorber for protection, thermochromic material for color change in coatings.

It is further contemplated that microcapsules of the present application can be used in incorporating actives of paper, mining industry, water treatment, adhesives, sealants, inks and dyes onto different substrate surfaces such as skin, hair, or textiles. Also contemplated are automotive applications including such encapsulated coolant systems, encapsulated lubricant additives such as anti-wear additives in engine oils and encapsulated UV absorbers for car coatings.

According to one non-limiting embodiment of the present application, the microcapsules of the present application can be prepared by a process comprising the steps of: (A) preparing an oil phase comprising: (i) a monomer mixture consisting essentially of: (a) greater than 70 to about 99% by weight of at least one polyfunctional ethylenically unsaturated monomer, (b) about 1 to about 30% by weight of at least one unsaturated carboxylic acid monomer or its ester , and (c) about 0 to about 30% by weight of at least one vinyl monomer; and (ii) at least one lipophilic core material; (B) preparing a separate aqueous phase comprising at least one polymeric emulsion stabilizer and water; (C) adding oil phase of step (A) to the aqueous phase of step (B) under mechanical shear to form an oil-in-water emulsion; and (D) polymerizing the oil-in-water emulsion of the step (C) through radical polymerization employing at least one initiator to produce core-shell microcapsules comprising an entrapped lipophilic core material and a polymeric shell, wherein the core-shell microcapsules are suspended in water. The shell of the resultant microcapsule consists essentially of: (a) greater than 70 to about 99% by weight of polyfunctional ethylenically unsaturated monomer, (b) about 1 to about 30% by weight of unsaturated carboxylic acid monomer or its ester, and (c) about 0 to about 30% by weight of at least one vinyl monomer.

In one non-limiting embodiment, the polymeric emulsion stabilizer is selected from the group consisting of cationic cellulose derivatives, quaternized gums, polyethylene imine, cationic polyacrylates and acrylamides, gelatin, quaternized protein hydrolysates, quaternized amino silicones, colloidal silica, hydroxyethyl cellulose, polyvinyl pyrrolidone, poly vinyl alcohol, styrene copolymer with maleic anhydride or acrylic acid and combinations thereof.

In one non-limiting embodiment, the initiator for preparing the microcapsule is a thermal or redox initiator selected from the group consisting of dicetyl peroxydicarbonate, di(4-tert-butylcyclohexyl) peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azobis(2,4-dimethyl valeronitrile), 2,2'-azobis(isobutyronitrile), 1,1'-azobis(cyclohexane-1-carbonitrile), 2,2'azobis-(2-methylbutyronitrile), dimethyl 2,2'-azobis(2-methylpropionate), 2,2'-azobis([2-methyl-N-(2-hydroxyethyl) propionamide and combinations thereof.

According to one non-limiting embodiment, the microcapsules described herein have a mean particle size of about 1 to about 2000 an. Other ranges of particles size are about 1 to about 500 µm, about 501 to about 1000/µm, about 1001 to about 1500 µm, or about 1501 to about 2000 µm. According to another non-limiting embodiment, the microcapsules described herein have a mean particle size of 1 to about 50 µm, or 1 to 20 µm.

The following non-limiting examples further illustrate the certain aspects of the present application.

EXAMPLES

Example 1: Preparation of 70% by weight of PETA and 30% by weight of methacrylic acid shell:

This example illustrates a process of preparing microcapsules by encapsulating a Fruity Accord fragrance material.

An oil phase was prepared by diluting 101.1 g Fruity Accord (ex-Robertet) with 25.3 g of propylene glycol dicaprylate/caprate, followed by adding a monomer mixture comprising of 18.3 g of pentaerythritol triacrylate (PETA) and 7.8 g of methacrylic acid (MAA) to form an oil mixture, wherein 0.78 g of 2,2'azobis-(2-methylbutyronitrile) thermal initiator was dissolved in the oil mixture under mechanical stirring.

Separately, an aqueous phase was prepared by dissolving 3.6 g of polyvinyl alcohol into 282.8 g deionized water by heating to 80° C. to form a polymer solution. The dissolved polymer solution was then cooled back to room temperature.

The aqueous phase was transferred into a 600 ml beaker and to this was added the above prepared oil phase under a high shear mixer (Silverson LR5) to form an oil-in-water emulsion with a mean droplet particle sizes of around 20 microns. The formed oil-in-water emulsion was transferred to a 700 ml reaction flask submerged in a thermostatic bath and mechanically stirred. The emulsion was deoxygenated by bubbling nitrogen for 30 minutes. After, the de-oxygenation with nitrogen, the emulsion was heated up to 80° C. to induce thermal polymerization. The oil-in-water emulsion was left reacting for a total of 6 hours to form the microcapsule shell. Then, 0.3 g of 2,2'azobis-(2-methylbutyronitrile) was added to consume any residual impurities of the monomers.

The resulting microcapsule slurry was an aqueous slurry of microcapsules in water and the distinct microcapsules were clearly visible under a light microscope. Using Malvern Mastersizer 2000 analyzer, the formed microcapsules had a volume weighted mean particle size diameter of 17.9 microns.

Example 2 (Comparative Example): Fruity Accord microcapsules having polymer shell comprising of 20% weight tBAEMA and 80% weight BDDMA A comparative example was prepared by encapsulating the Fruity Accord fragrance material of Example 1 according to the disclosure of PCT patent application WO2012-075293. The experimental procedure used for preparing this comparative sample was described as follows:

An oil phase was prepared by diluting 101.1 g Fruity Accord with 25.3 g of Propylene glycol dicaprylate/caprate, followed by adding 17.5 g of 1,4-butanediol dimethacrylate (BDDMA) and 8.6 g of t-butylaminoethyl methacrylate (tBAEMA) to form an oil phase. An amount of 0.78 g of 2,2'azobis-(2-methylbutyronitrile), thermal initiator, was dissolved in the oil phase.

Separately, an aqueous phase was prepared by dissolving 3.6 g of polyvinyl alcohol into 282.8 g deionized water by heating to 80° C. and cooling back to room temperature.

The above oil phase was added to the aqueous phase under a high shear mixer (Silverson LR5) to form an oil-in-water emulsion having a mean particle size of 20 microns. The formed emulsion was transferred to a 700 ml reaction flask submerged in a thermostatic bath and mechanically stirred. The emulsion was deoxygenated by bubbling nitrogen for 30 minutes. After, the bubbling with nitrogen, the emulsion was warmed to 80° C. to induce thermal polymerization. The mixture was left polymerizing for total of 6 hours. Then, 0.3 g of 2,2'azobis-(2-methylbutyronitrile) was added to consume any residual impurities of the monomers.

The resulting microcapsule samples was an aqueous slurry of microcapsules in water with a volume weighted mean D [4,3] particle size diameter of 18.7 microns as measured by Malvern Mastersizer 2000 particle size analyzer.

Example 3 (Comparative Example): Fruity Accord microcapsules having melamine formaldehyde polymer shell This example references preparation of microencapsulated Fruity Accord fragrance material with a melamine-formaldehyde polymer shell. The reference microcapsules were prepared by in-situ polymerization of melamine formaldehyde precondensate precursor according to Example 12 (preparation of Sample B) described in PCT patent application WO2012-075293 but in this case 140 g of Fruity Accord was used instead of the dyed isopropyl myristate oil.

The resulting sample was an aqueous slurry of Fruity Accord microcapsules in water. Using Malvern Mastersizer 2000 analyzer, the microcapsules had a volume weighted mean particle size diameter of 19.0 microns.

Example 4: Olfactory Performance of Fragrance Microcapsules

The fragrance microcapsules of Examples 1, 2 and 3 were separately dosed into Ultra Downy Free & Gentle liquid fabric softener (P&G) at 0.35% fragrance material equivalents. Each of the three fabric softener formulations containing the respective microcapsules were then further split into two samples to allow storage at two different conditions; (i) 0 day at 23° C. and (ii) 4 weeks at 40° C.

After each storage period (0 day or 4 weeks), the corresponding fabric softener sample was subjected to laundry protocol wash tests using a standard US front load washing machine. The experimental procedure involved washing cotton terry towels by normal wash cycle and the test fabric softener was auto dispensed into the washer during the rinse cycle. The laundered towels were line dried overnight, bagged, labeled and evaluated by trained panelists. The fragrance evaluation involved blind, randomized, panel of 30 assessors. Each assessor rated the fragrance intensity from a scale ranging from 0 to 9 before and after rubbing the dried terry towel. A score of 0 suggest no odor, and a score rating of 9 indicates a very strong odor.

The olfactory performance results for the two different storage time/temperature samples are summarized in Table 1.

From the sensory performance score rating results given in Table 1, it is clearly apparent that fragrance microcapsules of the present invention (Example 1) have higher score rating than the corresponding controls (Samples from Example 2 and 3). After 4 week's fabric softener storage at 40° C. and on laundry testing the inventive microcapsules exhibit still strong fragrance intensities; score rating of 7. This clearly demonstrates both retention of fragrance materials and the desired olfactory performance in use. It is inferred that the comparative microcapsules (Examples 2 & 3) leak some fragrances in fabric softeners and hence do not give the required fragrance performance in use.

TABLE 1

Olfactory performance score rating of Fruity Accord microcapsules of Examples 1-3

| Microcapsule Sample | Fabric softener storage 0 Day at 23° C. | | Fabric softener storage 4 weeks at 40° C. | |
| --- | --- | --- | --- | --- |
| | Before rubbing | After rubbing | Before rubbing | After rubbing |
| Example 1-according to present invention | 4.0 | 7.0 | 3.0 | 7.0 |
| Comparative Sample of Example 2 | 2.5 | 5.0 | 1.0 | 1.0 |
| Comparative Sample of Example 3 | 2.0 | 3.0 | 1.0 | 1.0 |

Examples 5-10: Apple Accord and Floral Accord Fragrance Materials

The experimental procedure outlined in Examples 1-3 were repeated with two other fragrance materials; Apple Accord and Floral Accord respectively. Table 2 summarizes each example, fragrance material used and the polymer shell chemistry of the resulting microcapsules.

TABLE 2

Fragrance microcapsules details of Examples 5 to 10

| Example | Example Description | Fragrance material | Polymer Shell |
|---|---|---|---|
| 5 | According to invention | Apple Accord | 70/30; PETA/MAA |
| 6 | Comparative microcapsules | Apple Accord | 80/20; BDDMA/tBAEMA |
| 7 | Comparative microcapsules | Apple Accord | Melamine-formaldehyde |
| 8 | According to invention | Floral Accord | 70/30; PETA/MAA |
| 9 | Comparative microcapsules | Floral Accord | 80/20; BDDMA/tBAEMA |
| 10 | Comparative microcapsules | Floral Accord | Melamine-formaldehyde |

Following the same procedure and laundry testing protocol outlined in Example 4, the fragrance microcapsules of Example 5 to 10 were separately dosed into Ultra Downy Free & Gentle liquid fabric softener (P&G) at 0.35% fragrance equivalents respectively. Each of the respective fabric softener formulations containing the respective microcapsules were then further split into two samples to allow storage at two different conditions before laundry olfactory evaluation.

Table 3 summarizes the olfactory performance results of the microcapsules of Example 5 to 10 from fabric softener after storage of the respective formulations at 0 days at 23° C. and after 4 weeks at 40° C.

TABLE 3

Performance score rating of microcapsules prepared with Apple & Floral Accords

| Microcapsule Sample | Fabric softener storage 0 Days at 23° C. | | Fabric softener storage 4 weeks at 40° C. | |
|---|---|---|---|---|
| | Before rubbing | After rubbing | Before rubbing | After rubbing |
| Example 5 | 3 | 7 | 2 | 5 |
| Comparative Example 6 | 1 | 4 | 1 | 1 |
| Comparison Example 7 | 1 | 1 | 1 | 2 |
| Example 8 | 2 | 7 | 2 | 6 |
| Comparative Example 9 | 1 | 4 | 2 | 2 |
| Comparative Example 10 | 2 | 2 | 1 | 2 |

From Table 3 sensory score rating, the inventive microcapsules of Example 5 and Example 8 provide still good olfactory performance after prolonged storage of the microcapsules in fabric softener base, whereas, the comparative microcapsules give some olfactory performance initially but lose their efficacy on storage of fabric softener formulations after 4 week's storage at 40° C. demonstrating the retention of fragrance material in fabric softener formulations and desired release from laundered terry towels.

Example 11: Preparation of microcapsules having polymer shell composition of 70% PETA, 15% methacrylic acid and 15% acrylic acid An oil phase was prepared by diluting 101.1 g Floral Accord with 25.3 g of mineral white oil, followed by adding monomer mixture comprising of 18.3 g of pentaerythritol triacrylate (PETA), 3.9 g of methacrylic acid (MAA) and 3.9 g of acrylic acid. To the resulting oil mixture was dissolved 0.78 g of 2,2'azobis-(2-methylbutyronitrile) thermal initiator under mechanical stirring.

Separately, an aqueous phase was prepared by dissolving 3.6 g of polyvinyl alcohol into 282.8 g deionized water by heating to 80° C. The dissolved polymer solution was then cooled back to room temperature (approximately 20° C.). The aqueous phase was transferred into a 600 ml beaker and then added the above prepared oil phase under a high shear mixer (Silverson LR5) to form an oil-in-water emulsion. The formed oil-in-water emulsion was transferred to a 700 ml reaction flask submerged in a thermostatic bath and mechanically stirred. The emulsion was deoxygenated by bubbling nitrogen for 30 minutes. After de-oxygenation the emulsion was warmed to 80° C. to induce thermal polymerization. The oil-in-water suspension was left reacting for a total of 6 hours to form the microcapsule shell. Then, 0.3 g of 2,2'azobis-(2-methylbutyronitrile) was added to consume any residual impurities.

The resulting product was an aqueous suspension of microcapsules in water. Under light microscope, distinct microcapsules are clearly visible having mean particle size diameter 26 microns. On application of pressure on the microscope slide cover slip, the microcapsule ruptured to release encapsulated fragrance material.

Example 12: Preparation of microcapsules having polymer shell comprising of 80% weight PETA and 20% weight MAA and encapsulating Personal Care Fragrance Accord (PC Accord)

Example 1 above was followed except the oil phase comprised of 101.1 g Personal Care Fragrance Accord (PC Accord) with 25.3 g of Propylene glycol dicaprylate/caprate, 20.9 g of pentaerythritol triacrylate (PETA), 5.2 g of methacrylic acid (MAA) and 0.78 g of 2,2'azobis -(2-methylbutyronitrile) thermal initiator.

The resulting sample was an aqueous slurry of microcapsules in water. The volume weighted mean particle sizes of the microcapsules was determined to be 19.9 microns.

Example 13: Olfactory performance of Example 12 microcapsules from Hair formulations (i) Leave-in Conditioner and (ii) Styling Gel The Personal Care Accord microcapsules of Example 12 were formulated separately into two consumer formulations; (i) a leave-in hair conditioner composition and a hair styling gel are given below.

Leave-in hair conditioner composition containing PC Accord microcapsules

| Material | % Weight |
|---|---|
| Behenyl trimethyl ammonium methosulfate + cetyl alcohol | 6.00 |
| Stearyl alcohol | 3.00 |
| Olive oil | 1.00 |
| PC Accord Microcapsules of Example 12 | 1.50 |
| Glycerine | 1.00 |
| DMDM Hydantoin | 0.10 |
| Water | q. s. ad 100% |

Hair styling gel composition containing PC Accord microcapsules

| Material | % Weight |
|---|---|
| Disodium EDTA | 0.05 |
| Amino methyl Propanol | 0.03 |
| Crosslinked poly(acrylic acid) | 0.60 |

-continued

| Material | % Weight |
|---|---|
| Acrylic Acid Copolymer | 0.25 |
| Polyvinylpyrrolidone | 2.00 |
| PC Accord Microcapsules of Example 12 | 1.50 |
| Propylene glycol, diazolidinyl urea & Iodopropynl butycarbamate | 0.50 |
| Water | 95.07 |

Both hair formulations of above were stored at 50° C. for 1 day and 43 days before testing on hair tresses separately following a standard hair testing protocol.

Hair tresses (9 g) were first washed with shampoo, rinsed for 30 seconds under tap water at 37° C. before applying 0.5 g of the respective hair formulation. The hair tresses were left to dry in a controlled temperature/humidity conditions (23° C.±2 & 50%±5) overnight before olfactory evaluation.

The intensity of the perception of the PC Accord on the hair tresses was evaluated by a panel of 6 panelists. Each panelist rating the hair tresses fragrance intensities before and rubbing; intensity rated on a scale ranging from 1 to 7. Where 1 score rating equates to no odor and 7 equates to very strong odour. The olfactory performance of the two aged hair products is summarized in the Table 4.

TABLE 4

Fragrance performance from hair formulations after 1 & 43 days at 50° C.

| Consumer Hair Product | Formulation storage for 1 day at 50° C. | | Formulation storage 43 days at 50° C. | |
|---|---|---|---|---|
| | Before rubbing | After rubbing | Before rubbing | After rubbing |
| Leave-in conditioner | 2.2 | 4.8 | 2.2 | 3.8 |
| Hair styling gel | 2.1 | 4.6 | 2.1 | 3.2 |

From the sensory results summarized in Table 6 it is inferred that the fragrance material is retained within the microcapsules in each hair compositions and subsequent on rubbing the hair tresses delivering the required fragrance bloom.

Example 14: Powdered form microcapsules

This example illustrated that dried powdered form of fragrance microcapsules can be produced by subjecting the aqueous slurry product to a spray drying process.

The aqueous dispersion of Example 1 was spray dried using Buchi Mini-Spray Drier B-290 with inlet temperature of 190° C. and outlet temperature of 95° C. The recovered product was a free flowing powder. This can be formulated in anhydrous and non-aqueous formulations.

Example 15: Encapsulation of an Epoxy compound (Neopentyl glycol diglycidyl ether)

An oil phase was prepared by dissolving 0.2 g of the initiator 2,2'azobis-(2-methylbutyronitrile) with 2.0 g of methacrylic acid (MAA) and 4.6 g of the cross-linker pentaerythritol triacrylate (PETA). 25.3 g of the di-epoxide compound (neopentyl glycol di-epoxide) was then added to the oil phase. The resulting oil phase was added to the aqueous phase comprising of 45.5 g deionized water and 6.9 g of polyvinyl alcohol. The emulsion was allowed to stir for 5 minutes, to form a coarse pre-emulsion. The emulsion was then homogenized using a high shear mixer (Silverson LR5) to form an oil-in-water emulsion with a mean particle oil droplet size of 15-20 microns. The fine emulsion was transferred to a 1-litre reactor flask, degassed with nitrogen at room temperature for 30 min and warmed to 80° C. for 6 hours.

The resulting microcapsule suspension was an aqueous suspension of microcapsules in water and was found to have a mean particle size of 20 microns under a light microscope.

The dry microcapsules, which were dried from the aqueous slurry in an oven, were mixed with a di-amine in order to determine the reactivity of encapsulated di-epoxide compound. In parallel, the dry capsules were broken using shear and subsequently mixed with the same di-amine compound. In the absence of shear, i.e. the capsules were not broken, no significant reaction was observed. On the other hand, once the capsules were broken a hardened material was discovered proposing a reaction had occurred between the encapsulated di-epoxide compound and the added di-amine Example 16: Encapsulation of a UV Sunscreen (octocrylene)

An oil phase was prepared by dissolving 1.31 g of 2,2'azobis-(2-methylbutyronitrile) thermal initiator into a monomer mixture comprising of 10.6 g methacrylic acid and 24.9 g of pentaerythritol triacrylate (PETA) crosslinking monomer. To this monomer mixture was dissolved 320.1 g of octocrylene (UV sunscreen). The resulting oil phase was added to an aqueous phase comprising of 13.6 g of polyvinyl alcohol and 428.9 g deionized water under a high shear mixer (Silverson LR5) to form an oil-in-water emulsion having mean particle oil droplets of around 3 microns.

The formed oil-in-water emulsion was transferred to a 1-litre reactor flask, then deoxygenated with nitrogen and warmed to 85° C. for 6 hours to form the microcapsules.

The resulting product formed is an aqueous suspension of microcapsules having encapsulated octocrylene. Under a light microscope, individual microcapsules are clearly observed with particle sizes of around 3 microns.

Following are non-limiting examples of consumer formulations containing microcapsules of the present invention.

Example 17: Microcapsules in fabric softener

Fabric Softener Composition

| Material | % Weight |
|---|---|
| Cationic surfactant (Esterquat) | 6.20 |
| Cationic rheology modifier (Jaypol ®213) | 0.65 |
| Phosphoric acid | 0.045 |
| Fragrance Microcapsules of Example 1 | 2.50 |
| Preservative/Dye | q.s. |
| Deionised Water | q.s. ad 100% |

Example 18: Microcapsules in hair conditioner

Hair Conditioner Composition

| Material | % Weight |
|---|---|
| Disodium EDTA | 0.02 |
| Hydroxyethyl cellulose | 0.50 |

-continued

| Material | % Weight |
| --- | --- |
| Butyrospermum Parkii (Shea Butter) | 10.00 |
| Caprylic/Capric Triglyceride | 5.00 |
| Cetearyl Alcohol (and) Behenyl Alcohol (and) Hydroxyethyl Cetearamidopropyldimonium Chloride | 5.00 |
| Cetearyl alchol | 3.00 |
| 2-hydroxyethyl-dimethyl-[3-[[2R,3S,4R,5R)-2,3,4,5,6-pentahydroxyhexanoyl]amino]propyl]azanium chloride (and) 3-(D-Gluconoyl-amino)propyl(2-hydroxyethyl)dimethyl-ammonium chloride | 2.00 |
| Fragrance microcapsules of Example 12 | 2.50 |
| Preservative | q.s. |
| Deionised water | q.s. ad 100% |

Example 19: Microcapsules in shower-rinse off product

Body Rinse Off Product Composition

| Material | % Weight |
| --- | --- |
| Glycerin | 30.0 |
| Disodium EDTA | 3.00 |
| Lightly crosslinked acrylates copolymer | 0.10 |
| Aqueous solution of Sodium Lauryl (1EO) Sulfate @ 25% | 48.0 |
| Sodium hydroxide @ 10% | 1.20 |
| Cocamidopropyl betaine | 8.00 |
| Sodium chloride @ 25% | 0.02 |
| Glycine based preservative | 0.50 |
| Fragrance Microcapsules of Example 12 | 3.75 |
| Preservative/Dye | q.s. |
| Deionised water | q.s. ad 100% |

Example 20: Microcapsules in antiperspirant/deodorant formulation

Antiperspirant/Deodorant Application—Aerosol Formulation

| Material | % Weight |
| --- | --- |
| Cyclomethicone | 14.25 |
| Diisopropyl Adipate | 4.50 |
| Disteardimonium Hectorite | 0.25 |
| Propylene Carbonate | 0.25 |
| Aluminum Chlorohydrate | 5.00 |
| Spray Dried Fragrance Microcapsules of Example 14 | 0.75 |
| Isobutane (and) propane propellant | 75.00 |
| Total | 100.00 |

Example 21: Microcapsules in Antiperspirant Stick

Antiperspirant Stick Composition

| Material | % Weight |
| --- | --- |
| Aluminium chlorohydrate | 20.00 |
| Cetyl alcohol | 18.00 |
| Stearic acid | 18.00 |

-continued

| Material | % Weight |
| --- | --- |
| Poly vinylpyrrolidone | 1.00 |
| Spray dried microcapsules of Example 12 | 2.00 |
| Cyclopentasilixane | q.s. ad 100% |

While a number of embodiments of this invention have been represented, it was apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

What is claimed is:

1. A microcapsule comprising:
   i. a lipophilic core comprising a lipophilic core material, and
   ii. a friable and highly crosslinked microcapsule shell; wherein said microcapsule shell is formed from oil-in-water emulsion polymerisation of a monomer mixture consisting essentially of: (a) greater than 70 to about 99% by weight of pentaerythritol triacrylate (PETA) (b) about 1 to about 30% by weight of at least one unsaturated carboxylic acid monomer or its ester selected from the group consisting of acrylic acid, methacrylic acid, maleic acid, maleic anhydride, fumaric acid, itaconic acid, 2-carboxylethyl acrylate, C1-C24 alkyl ester of acrylic acid, C1-C24 alkyl ester of methacrylic acid, and combinations thereof, and (c) about 0 to about 30% by weight of at least one vinyl monomer selected from the group consisting of N-vinyl pyrrolidone, N-vinyl caprolactam, 2-hydroxylethyl pyrrolidone methacrylate, octyl acrylamide, acryloxyethyltrimethyl ammonium chloride, 2-hydroxyethyl methacrylate and combinations thereof; and
   wherein the lipophilic core is encapsulated by the friable and highly crosslinked microcapsule.

2. The microcapsule according to claim 1, wherein said lipophilic core material is selected from the group consisting of fragrances, UV absorbers, emollient oils, insecticides, dyes, detergents, printing inks, perfumes, silicone conditioners, hair treatment/shampoo materials, biocides, adhesives, corrosion inhibitors, anti-fouling agents, flavors, cosmetic & personal care actives, oxidizing agents, pharmaceutical agents, agrochemicals/pesticides, lipids/fats, food additive, liquid crystals, coating materials. catalysts, preservatives and/or antimicrobial agents, lipophilic scale inhibitors, chemical reactants, rustproofing agents, recording materials, magnetic substances, and combinations thereof.

3. The microcapsule according to claim 1, wherein the friable and highly crosslinked microcapsule shell is formed from a monomer mixture consisting essentially of methacrylic acid and/or acrylic acid and pentaerythritol triacrylate (PETA).

4. The microcapsule according to claim I. wherein said unsaturated carboxylic acid monomer or its ester is present in an amount from about 10 to about 30% by weight of total monomers in polymer shell.

5. The microcapsule according to claim 1, wherein the friable and highly crosslinked microcapsule provides both retention and release of the lipophilic core material.

6. The microcapsule according to claim 1, wherein said microcapsule has a mean particle size of 1-2000 μm.

7. A process for preparing microcapsules comprising the steps of:
A. preparing an oil phase comprising:
   i. a monomer mixture consisting essentially of: (a) greater than 70 to about 99% by weight of pentaerythritol triacrylate (PETA) (b) about 1 to about 30% by weight of at least one unsaturated carboxylic acid monomer or its ester selected from the group consisting of acrylic acid, methacrylic acid, maleic acid, maleic anhydride, fumaric acid, itaconic acid, 2-carboxylethyl acrylate, C1-C24 alkyl ester of acrylic acid, C1-C24 alkyl ester of methacrylic acid, and combinations thereof, and (c) about 0 to about 30% by weight of at least one vinyl monomer selected from the group consisting of N-vinyl pyrrolidone, N-vinyl caprolactam, 2-hydroxylethyl pyrrrolidone methacrylate, octyl acrylamide, acryloxyethyltrimethyl ammonium chloride, 2-hydroxyethyl methacrylate and combinations thereof, and
   ii. at least one lipophilic core material;
B. preparing a separate aqueous phase comprising at least one polymeric emulsion stabilizer and water;
C. adding the oil phase of step (A) to the aqueous phase of step (B) under mechanical shear to form an oil-in-water emulsion;
D. polymerizing the oil-in-water emulsion of step (C) through radical polymerisation by heating the emulsion to at least 80° C. and employing at least one initiator to produce core-shell microcapsules comprising an entrapped lipophilic core material and a friable and highly crosslinked polymer shell to result in a suspension of core-shell microcapsules in water.

8. The process according to claim 7, wherein the shell of the microcapsule consists essentially of: (a) greater than 70 to about 99% by weight of pentaerythritol triacrylate (PETA), (b) about 1 to about 30% by weight of at least one unsaturated carboxylic acid monomer or its ester, and (c) about 0 to about 30% by weight of at least one vinyl monomer.

9. The process according to claim 7, wherein the polymeric emulsion stabilizer is selected from the group consisting of cationic cellulose derivatives, quaternized gums, polyethylene imine, cationic polyacrylates and acrylamides, gelatin, quaternized protein hydrolysates, quaternized amino silicones, colloidal silica, hydroxyethyl cellulose, polyvinyl pyrrolidone, poly vinyl alcohol, styrene copolymer with maleic anhydride or acrylic acid, and a combination thereof.

10. The process according to claim 7, wherein the initiator is a theimal or redox initiator selected from the group consisting of dicetyl peroxydicarbonate, di(4-tert -butylcyclohexyl)peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azob is (2,4-dimethyl valeronitrile), 2,2'-azob is (is obutyronitrile), 1,1'-azob is (cyclohexane-1-carbonitrile), 2,2'azobis-(2-methylbutyronitrile), dimethyl 2,2'-azobis(2-methylpropionate), 2,2'-azobis[2-methyl-N-(2-hydroxyethyl) propionamide, and combinations thereof.

11. A consumer care composition comprising a microcapsule comprising: (i) a lipophilic core comprising a lipophilic core material, and (ii) a friable and highly crosslinked microcapsule shell, wherein said microcapsule shell is formed from oil-in-water emulsion polymerisation of a monomer mixture consisting essentially of (a) greater than 70 to about 99% by weight of pentaerythritol triacrylate (PETA) (b) about 1 to about 30% by weight of at least one unsaturated carboxylic acid monomer or its ester selected from the group consisting of acrylic acid, methacrylic acid, maleic acid, maleic anhydride, fumaric acid, itaconic acid, 2-carboxylethyl acrylate, C1-C24 alkyl ester of acrylic acid, C1-C24 alkyl ester of methacrylic acid, and combinations thereof, and (c) about 0 to about 30% by weight of at least one vinyl monomer selected from the group consisting of N-vinyl pyrrolidone, N-vinyl caprolactam, 2-hydroxyle thyl pyrrrolidone methacrylate, octyl acrylamide, acryloxyethyltrimethyl ammonium chloride, 2-hydroxyethyl methacrylate and combinations thereof;
wherein the lipophilic core is encapsulated by the friable and highly crosslinked microcapsule shell.

12. The consumer care composition according to claim 11, wherein said consumer care composition is a laundry care composition, a personal care composition, an all-purpose cleaner composition, a therapeutic composition, a cosmetic composition, a homecare & cleaning composition, pharmaceutical or cosmeceutical composition.

13. The consumer care composition according to claim 12, wherein said personal care composition is a hair shampoo, hair conditioner, rinse off or leave on composition for skin and hair, hair rinse, hair styling gel, hair colorant, hair removal depilatory, antiperspirant/deodorant, hand sanitizer, hand cream, hand lotion, liquid/solid soap, shower gel, body lotion, bar soap, body wash, sun protection product, preservative composition, sun and tissue regeneration scaffold, oral care, toothpaste, mouth wash and chewing gum, denture adhesive or dental care.

14. The consumer care composition according to claim 12, wherein the laundry care composition is a rinse conditioner, a liquid detergent, a solid detergent or a fabric refresher.

15. The consumer care composition according to claim 12, wherein the personal care composition is formed as a stick, roll-on or aerosol spray.

16. The consumer care composition according to claim 12, wherein the home care composition is a household cleaner, a hard surface cleaner, a carpet cleaner, a polish, or a sprayable composition.

17. A method of using a microcapsule comprising employing said microcapsule as a delivery matrix to deliver lipophilic core materials for industrial compositions that are related to agrochemicals, textiles, paper, mining, oil industry, water treatment, adhesives. coatings, plastics, sealants, construction, paints, inks and dyes onto different substrate surfaces such as skin, hair, or textiles, and wherein said microcapsule comprises: (i) at least one lipophilic core comprising a lipophilic core material, and (ii) a friable and highly crosslinked microcapsule shell, wherein said microcapsule shell is formed from oil-in-water emulsion polymerisation of a monomer mixture consisting essentially of: (a) greater than 70 to about 99% by weight of pentaerythritol triacrylate (PETA) (b) about 1 to about 30% by weight of at least one unsaturated carboxylic acid monomer or its ester selected from the group consisting of acrylic acid, methacrylic acid, maleic acid, maleic anhydride, fumaric acid, itaconic acid, 2-carboxylethyl acrylate, C1-C24 alkyl ester of acrylic acid, C1-C24 alkyl ester of methacrylic acid, and combinations thereof, and (c) about 0 to about 30% by weight of at least one vinyl monomer selected from the group consisting of N-vinyl pyrrolidone, N-vinyl caprolactam, 2-hydroxylethyl pyrrrolidone methacrylate, octyl acrylamide, acryloxyethyltrimethyl ammonium chloride, 2-hydroxyethyl methacrylate and combinations thereof;

wherein the lipophilic core is encapsulated by the friable and highly crosslinked microcapsule shell.

\* \* \* \* \*